United States Patent [19]

Watkins

[11] Patent Number: 4,914,090

[45] Date of Patent: Apr. 3, 1990

[54] OPHTHALMIC COMPOSITIONS

[75] Inventor: Robert W. Watkins, Great Meadows, N.J.

[73] Assignee: Schering Corporation, Kenilworth, N.J.

[21] Appl. No.: 793,929

[22] Filed: Nov. 1, 1985

[51] Int. Cl.$^4$ .............................................. A61K 31/56
[52] U.S. Cl. ..................................... 514/171; 514/913
[58] Field of Search ................................ 514/171, 913

[56] References Cited

U.S. PATENT DOCUMENTS

| | | | |
|---|---|---|---|
| 3,892,857 | 7/1975 | Difazio et al. | 514/174 |
| 3,980,778 | 9/1976 | Ayer et al. | 514/171 |
| 4,124,707 | 11/1978 | Green et al. | 514/179 |
| 4,442,089 | 4/1984 | Horovitz | 384/173 |
| 4,472,393 | 9/1984 | Shapiro | 514/172 |
| 4,474,751 | 10/1984 | Haslam et al. | 514/171 |

FOREIGN PATENT DOCUMENTS 114333 12/1983 European Pat. Off. .

OTHER PUBLICATIONS

T. Csaky et al., ed., *Cutting's Handbook of Pharmacology*, 7th ed. pp. 404–415.
*Ann. Rev. Biochem.*, 51 (1982), 283–308.
M. Wyvratt et al., *Medicinal Res. Rev.*, 5 (1985) pp. 483–531 *The Physician's Desk Reference*, 1984 ed., p. 998.

*Primary Examiner*—Douglas W. Robinson
*Assistant Examiner*—Zchreh A. Fay
*Attorney, Agent, or Firm*—Anita W. Magatti; Stephen I. Miller; Gerald S. Rosen

[57] ABSTRACT

The use of an angiotensin converting enzyme inhibitor for reducing and controlling the elevation of intraocular pressure associated with the use of corticosteroids is disclosed. Also disclosed are the use of the combination of an angiotensin converting enzyme inhibitor and a steroid, and pharmaceutical compositions comprising the combination.

5 Claims, No Drawings

OPHTHALMIC COMPOSITIONS

SUMMARY OF THE INVENTION

The present invention relates to the use of angiotensin converting enzyme (ACE) inhibitors in treating the rise in intraocular pressure (IOP) associated with ophthalmic and systemic use of steroidal anti-inflammatory drugs.

A second aspect of the invention is the use of a combination of an ACE inhibitor and an anti-inflammatory steroid, wherein the ACE inhibitor suppresses the effect of the steroid-induced rise in IOP.

The invention also relates to topical opthalmic compositions comprising ACE inhibitors and steroidal anti-inflammatory agents.

BACKGROUND

Steroidal anti-inflammatory drugs are commonly prescribed for inflammatory conditions such as arthritis, and for treatment of ocular inflammation due to mechanical or chemical irritants or immunological reactions resulting from such conditions as allergic conjunctivitis, herpes zoster keratitis, iritis, and corneal injury from chemical or thermal burns or penetration of foreign bodies. Anti-inflammatory steriods, however, are known to cause an elevation in IOP resulting in the condition known as ocular hypertension. While the term "ocular hypertension" indicates elevated IOP without optic nerve head damage or loss of vision, the condition is believed by the majority of ophthalmologists to represent the earliest phase in the onset of glaucoma, which is characterized by optic nerve damage and loss of vision, and which may lead to blindness. Patients with pre-existing glaucoma are particularly vulnerable to additional elevations in IOP caused by steroidal anti-inflammatory therapy. Also, in some susceptible individuals, topical steroids can induce an intractable glaucoma.

The increase in IOP often associated with the topical optical administration of steroidal anti-inflammatory agents can occur with all modes of administration of the drugs, including systemic (usually oral), local injection (e.g., depot injection), topical, aerosol or intravitreal administration.

Anti-inflammatory steroids include hydrocortisone, cortisone, prednisolone, prednisone, dexamethasone, methylprednisolone, triamcinolone, betamethasone, alclometasone, flunisolide, beclomethasone, clorocortolone, diflorasone, halcinonide, fluocinonide, flucinolone, desoximetasone, medrysone, paramethasone, 9,21-dichloro-17-[(2-furanylcarbonyl)oxy]-11-hydroxy-16α-methyl-pregna-1,4-diene-3,20-dione, and fluoromethalone, and their pharmaceutically acceptable salts and esters.

Drugs currently employed to treat glaucoma, e.g., epinephrine and pilocarpine, are not particularly effective in lowering steroid-induced increases in IOP, and often produce serious side effects.

DETAILED DESCRIPTION OF THE INVENTION

The elevation in IOP associated with the clinical ophthalmic and systemic use of anti-inflammatory steroids, in particular corticosteroids, can be reduced by the administration of an angiotensin converting enzyme (ACE) inhibitor. The ACE inhibitor may be administered separately from the steroid treatment in order to lower elevated IOP, or may be co-administered with the steroid to supress the IOP-raising effect of the steroid while not interfering with the anti-inflammatory activity of the steroid.

The present invention therefore relates to a method for reducing and controlling the elevated IOP associated with the ophthalmic and systemic use of steroidal anti-inflammatory agents, which method comprises administering to a mammal in need of such treatment an effective amount of an ACE inhibitor, preferably in a ophthamologically acceptable topical carrier.

In addition, the present invention relates to a method for supressing the elevation in IOP associated with the ophthalmic and systemic use of steroidal anti-inflammatory agents, which method comprises administering to a mammal in need of such treatment a combination of an anti-inflammatory effective amount of a steroid and an effective amount of an ACE inhibitor, either separately or in the same pharmaceutical composition.

Any possible combination of dosage forms may be used to administer the combination, e.g., oral steroid/topical ACE inhibitor, topical steroid/oral ACE inhibitor, oral steroid/oral ACE inhibitor, topical steroid/topical ACE inhibitor, and locally injected steroid/topical Ace inhibitor. A preferred combination comprises a steroid and a topical ACE inhibitor. For ophthalmic use, a combination of a topical steroid and a topical ACE inhibitor is preferred.

A third aspect of the invention relates to a pharmaceutical composition comprising both a steroid and an ACE inhibitor. Preferred is a topical ophthalmic pharmaceutical dosage form comprising both a steroid and an ACE inhibitor.

The steroids contemplated for use in this invention are exemplified by, but are not limited to, those listed above. Preferred steroids are hydrocortisone, prednisolone, dexamethasone, betamethasone, beclomethasone, medrysone and fluoromethalone, and their pharmaceutically acceptable salts and esters.

Examples of angiotensin converting enzyme (ACE) inhibitors are those disclosed in the following patents and published patent application:

U.S. Pat. No. 4,105,776 to Ondetti et al discloses proline derivatives which are angiotensin converting enzyme (ACE) inhibitors and have the general formula

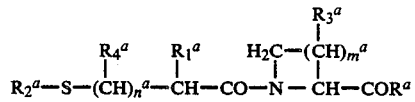

wherein
$R^a$ is hydroxy, $NH_2$ or lower alkoxy;
$R_1^a$ and $R_4^a$ is hydrogen, lower alkyl, phenyl or phenyl-lower alkyl;
$R_2^a$ is hydrogen, lower alkyl, phenyl, substituted phenyl wherein the phenyl substituent is halo, lower alkyl or lower alkoxy, phenyl-lower alkyl, diphenyl-lower alkyl, triphenyl-lower alkyl, lower alkylthiomethyl, phenyl-lower alkylthiomethyl, lower alkanoly-amidomethyl,

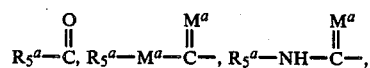

$R_6{}^a$—S—, or $R_7{}^a$;
$R_3{}^a$ is hydrogen, hydroxy or lower alkyl;
$R_5{}^a$ is lower alkyl, phenyl or phenyl-lower alkyl;
$R_6{}^a$ is lower alkyl, phenyl, substituted phenyl (wherein the phenyl substituent is halo, lower alkyl or lower alkoxy), hydroxy-lower alkyl or amino(carboxy)lower alkyl;

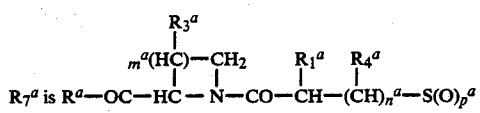

$M^a$ is O or S;
$m^a$ is 1 to 3;
$n^a$ and $p^a$ each is 0 to 2.

European patent application No. 97050 published Dec. 28, 1983 discloses phosphinylalkanoyl substituted prolines which have the formula

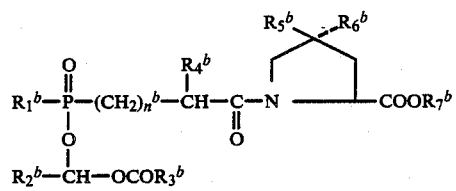

$R_1{}^b$ is alkyl, aryl, aralkyl, cycloalkyl or cycloalkylalkyl;
$R_2{}^b$ is cycloalkyl, 3-cyclohexenyl or 2-alkyl-3-cyclohexenyl;
$R_3{}^b$ is alkyl, cycloalkyl or phenyl;
$R_4{}^b$ is H or alkyl;
One of $R_5{}^b$ and $R_6{}^b$ is H and the other is alkyl-$X^b$-, phenyl-$X^b$-alkoxy, phenoxy, phenyl, cycloalkyl, alkyl or phenylalkyl; or
$R_5{}^b$ and $R_6{}^b$ together form —$X^b$CH$_2$CH$_2$X$^b$—, $X^b$ is S, SO or SO$_2$;
$R_7{}^b$ is H or CH($R_2{}^b$)OCOR$_3{}^b$;
$n^b$ is 0 or 1;
'aryl' is phenyl opt. substituted by halo, alkyl, alkoxy, alkylthio, OH, alkanoyl, NO$_2$, amino, dialkylamino and/or CF$_3$; alkyl has 1–10C, cycloalkyl 3–7C, alkoxy 1–8C and alkanoyl 2–9C.

European patent application No. 83172 published July 6, 1983 discloses N-substituted acetyl-L-proline derivatives which are said to be angiotensin converting enzyme inhibitors and have the formula

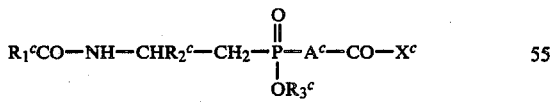

$R_1{}^c$ and $R_2{}^c$ are H, 1–7C alkyl, 1–7C haloalkyl, (Ch$_2$)$_m{}^c$—D$^c$, 1–7C aminoalkyl or a group of formula:

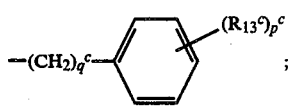

$D^c$ is cycloalkyl, furyl, thienyl or pyridinyl;

$A^c$ is (CH$_2$)$_n$—CHR$_{21}{}^c$, NR$_{22}{}^c$—CHR$_{23}{}^c$ or O—CHR$_{23}{}^c$;
$n^c$ is 0 or 1;
$q^c$ is 0–7;
$R_{21}{}^c$ is H, 1–7C alkyl, 1–7C haloalkyl, benzyl or phenethyl;
$R_{22}{}^c$ is H, 1–7C alkyl;
$R_{23}{}^c$ is H, 1–7C alkyl, 1–7C haloalkyl or (CH$_2$)$_r{}^c$D$_1{}^c$;
$D_1{}^c$ is phenyl, 4-hydroxyphenyl, 3,4-dihydroxyphenyl, 3-indolyl, 4-imidazolyl, NH$_2$, SH, 1–7C alkylthio, guanidino or CONH$_2$;
$X^c$ is a group of formula (II)$^c$–(V)$^c$, or NR$_4{}^c$—CHR$_5{}^c$—COOR$_6{}^c$;

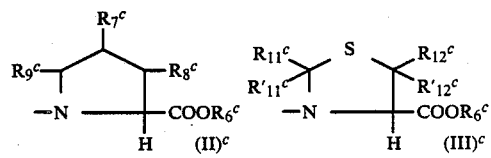

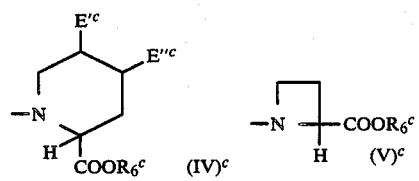

where
$R_9{}^c$ and $R_8{}^c$ are H and $R_7{}^c$ is as defined below;
$R_9{}^c$ and $R_7{}^c$ are H and $R_8{}^c$ is as defined below;
$R_7{}^c$ and $R_8{}^c$ are H and $R_9{}^c$ is as defined below;
$R_9{}^c$ and $R_8{}^c$ are H and —CHR$_7{}^c$— is replaced by —CR$_{10}{}^c$R$_{10}{}^c$;
$R_9{}^c$ is H and $R_7{}^c$+$R_8{}^c$ form a double bond;
$R_9{}^c$ is H and $R_7{}^c$+$R_8{}^c$ complete a fused benzene ring; or
$R_8{}^c$ is H and $R_9{}^c$+$R_7{}^c$ complete a fused benzene ring;
$E'^c$ and $E''^c$ are H or $E'^c$+$E''^c$ complete a fused benzene ring;
$R_7{}^c$ is H, 1–7C alkyl, halogen, keto, OH, 2–8C alkanoyl-amino, N$_3$, NH$_2$, NR$_{19}{}^c$R$_{20}{}^c$, (CH$_2$)$_m{}^c$—D, O—CONR$_{15}{}^c$R$_{15}{}^c$, 1–7C alkoxy, 1–7C alkylthio, or a group of formula (VI)$^c$, (VII)$^c$ or (VIII)$^c$:

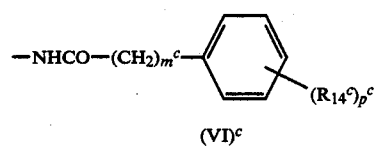

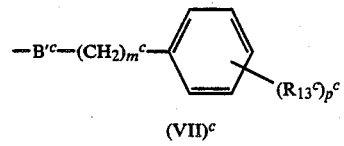

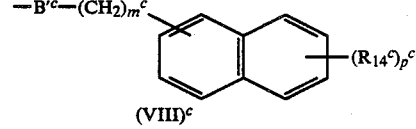

$B'^c$ is a bond or it is O or S; $R_8{}^c$ is keto, halogen, O—CONR$_{15}{}^c$R$_{15}{}^c$, 1–7C alkoxy, 1–7C alkylthio, or a group (VII)$^c$ or (VIII)$^c$ in which $B'^c$ is O or S;

$R_9{}^c$ is keto or a group $(VIII)^c$ in which $B'^c$ is a bond;
$R_{10}{}^c$ is halogen or $Y^c R_{16}{}^c$;
$R_{11}{}^c$, $R'_{11}{}^c$, $R_{12}{}^c$ and $R'_{12}{}^c$ are H or 1–7C alkyl, or $R_{11}{}^c$ is a group of formula $(IX)^c$ and the other 3 are H;

$R_{13}{}^c$ is H, 1–4C alkyl, 1–4C alkoxy, 1–4C alkylthio, Cl, Br, F, CF$_3$, OH, Ph, PhO, PhS or PhCH$_2$;
$R_{14}{}^c$ is H, 1–4C alkyl, 1–4C alkoxy, 1–4C alkylthio, Cl, Br, F, CF$_3$ or OH;
$m^c$ is 0–3;
$p^c$ is 1–3 but it is 2 or 3 only when $R_{13}{}^c$ or $R-^c$ is H, Me, MeO, Cl or F;
$R_{15}{}^c$ is H or 1–4C alkyl;
$Y^c$ is O or S;
$R_{16}{}^c$ is 1–4C alkyl or group $(VIII)^c$ in which $B'^c$ *is a bond; or the two* $R_{16}{}^c$ groups complete a 5- or 6-membered ring in which the C atoms may each bear 1 or 2 alkyls having 1–4C;
$R_4{}^c$ is H, 1–7C alkyl, cycloalkyl or (CH$_2$)$_{r^c}$Ph;
$R_5{}^c$ is H, 1–7C alkyl or (CH$_2$)$_{r^c}$—D$_1{}^c$;
$r^c$ is 1–4;
$R_3{}^c$ and $R_6{}^c$ are H, 1–7C alkyl, PhCH$_2$, PhCH or CHR$_{17}{}^c$—O—COR$_{18}{}^3$;
$R_{17}{}^c$ is H, 1–7C alkyl or Ph;
$R_{18}{}^c$ is H, 1–7C alkyl, 1–7C alkoxy or Ph; or $R_{17}{}^c + R_{18}{}^c$ form (CH$_2$)$_2$, (CH$_2$)$_3$, —CH=CH or o-phenylene;
$R_{19}{}^c$ is 1–7C alkyl, benzyl or phenethyl; and
$R_{20}{}^c$ is H or chosen as for $R_{19}{}^c$.

European patent application No. 0 012 401 published June 25, 1980 discloses carboxyalkyl dipeptide derivatives which are said to be angiotensin converting enzyme inhibitors and have the formula

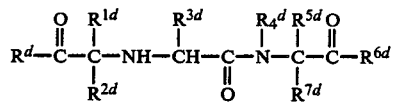

wherein
$R^d$ and $R^{6d}$ are the same or different and are hydroxy, lower alkoxy, lower alkenoxy, dilower alkylamino lower alkoxy (dimethylaminoethoxy), acylamino lower alkoxy (acetylaminoethoxy), acyloxy lower alkoxy (pivaloyloxymethoxy), aryloxy, such as phenoxy, arloweralkoxy, such as benzyloxy, substituted aryloxy or substituted arloweralkoxy wherein the substituent is methyl, halo or methoxy, amino, loweralkylamino, diloweralkylamino, hydroxyamino, arloweralkylamino such as benzylamino;
$R^{1d}$ is hydrogen, alkyl of from 1 to 20 carbon atoms which include branched and cyclic and unsaturated (such as allyl) alkyl groups, substituted loweralkyl wherein the substitutent can be halo, hydroxy, lower alkoxy, aryloxy such as phenoxy, amino, diloweralkylamino, acylamino, such as acetamido and benzamido, arylamino, guanidino, imidazolyl, indolyl, mercapto, loweralkylthio, arylthio such as phenylthio, carboxy or carboxyamido, carboloweralkoxy, aryl such as phenyl or naphthyl, substituted aryl such as phenyl wherein the substituent is lower alkyl, lower alkoxy or halo, arloweralkyl, arloweralkenyl, heteroarlower alkyl or heteroarlower alkenyl such as benzyl, styryl or indolyl ethyl, substituted arloweralkyl, substituted arloweralkenyl, substituted heteroarlower alkyl, or substituted heteroarlower alkenyl, wherein the substitutent(s) is halo, dihalo, lower alkyl, hydroxy, lower alkoxy, amino, aminomethyl, acylamino (acetylamino or benzoylamino) diloweralkylamino, loweralkylamino, carboxyl, haloloweralkyl, cyano or sulfonamido; arloweralkyl or heteroarloweralkyl substituted on the alkyl portion by amino or acylamino (acetylamino or benzoylamino);

$R^{2d}$ and $R^{7d}$ are the same or different and are hydrogen or lower alkyl;
$R^{3d}$ is hydrogen, lower alkyl, phenyl lower alkyl, aminomethyl phenyl lower alkyl, hydroxy phenyl lower alkyl, hydroxy lower alkyl, acylamino lower alkyl (such as benzoylamino lower alkyl, acetylamino lower alkyl), amino lower alkyl, dimethylamino lower alkyl, halo lower alkyl, guanidino lower alkyl, imidazolyl lower alkyl, indolyl lower alkyl, mercapto lower alkyl, lower alkyl thio lower alkyl;
$R^{4d}$ is hydrogen or lower alkyl;
$R^{5d}$ is hydrogen, lower alkyl, phenyl, phenyl lower alkyl, hydroxy phenyl lower alkyl, hydroxy lower alkyl, amino lower alkyl, guanidino lower alkyl, imidazolyl lower alkyl, indolyl lower alkyl, mercapto lower alkyl or lower alkylthio lower alkyl;
$R^{4d}$ and $R^{5d}$ may be connected together to form an alkylene bridge of from 2 to 4 carbon atoms, an alkylene bridge of from 2 to 3 carbon atoms and one sulfur atom, an alkylene bridge of from 3 to 4 carbon atoms containing a double bond or an alkylene bridge as above substituted with hydroxy, lower alkoxy, lower alkyl or dilower alkyl; and the pharmaceutically acceptable salts thereof.

U.S. Pat. No. 4,462,943 to Petrillo et al discloses carboxyalkyl amino acid derivatives of substituted prolines which are angiotensin converting enzyme inhibitors and have the formula

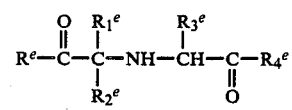

$R_4{}^e$ is a substituted proline of the formula

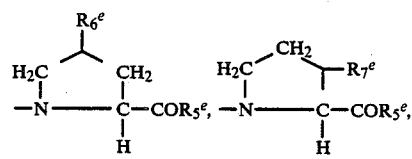

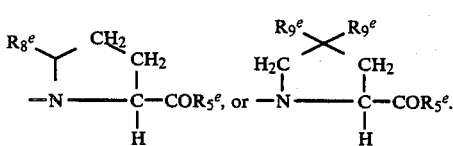

$R_6{}^e$ is halogen, keto, azido,

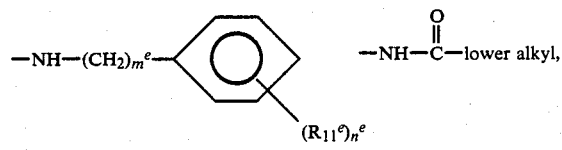 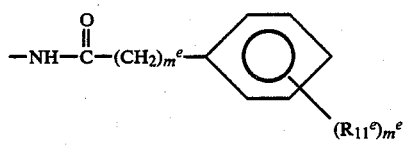 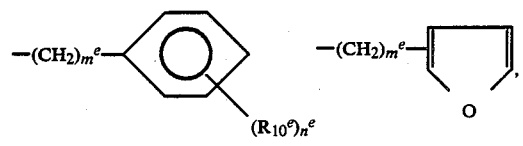 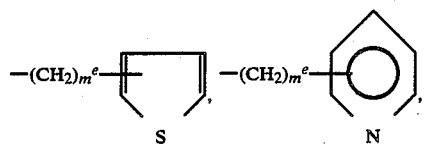

a 1- or 2-naphthyl of the formula

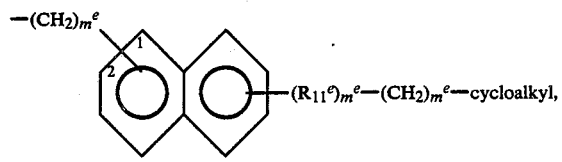

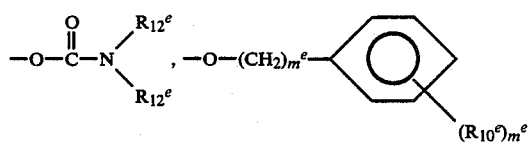

a 1- or 2-naphthyloxy of the formula

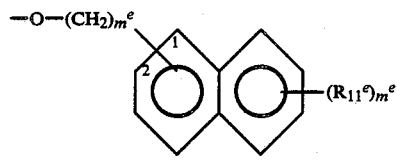

—S-lower alkyl,

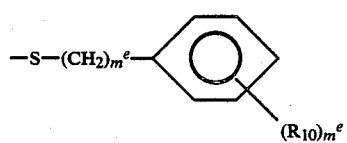

or a 1- or 2-naphthylthio of the formula

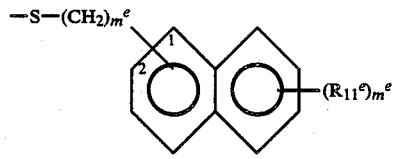

$R_7^e$ is keto, halogen,

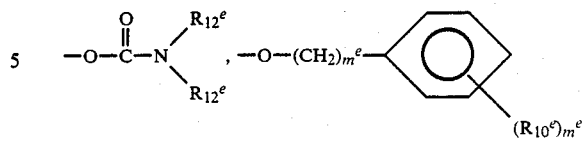

a 1- or 2-naphthloxy of the formula

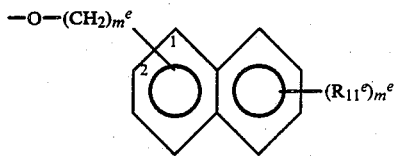

—S-lower alkyl,

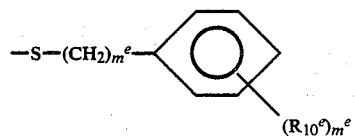

or a 1- or 2-naphthylthio of the formula

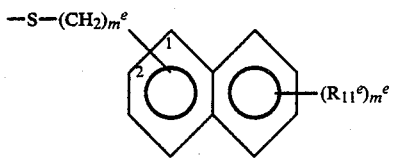

$R_8^e$ is keto or

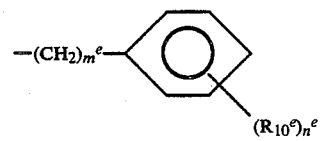

$R_9^e$ is halogen or $-Y^e-R_{13}^e$.

$m^e$ is zero, one, two, or three.

$R_{10}^e$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{11}^e$ is hydrogen, lower alkyl of 1 to 4 carbons, lower alkoxy of 1 to 4 carbons, lower alkylthio of 1 to 4 carbons, bromo, fluoro, trifluoromethyl, or hydroxy.

$n^e$ is one, two or three provided that $n^e$ is more than one only if $R_{10}^e$ or $R_{11}^e$ is hydrogen, methyl, methoxy, chloro, or fluoro.

$R_{12}^e$ is hydrogen or lower alkyl of 1 to 4 carbons.

$Y^e$ is oxygen or sulfur.

$R_{13}^e$ is lower alkyl of 1 to 4 carbons.

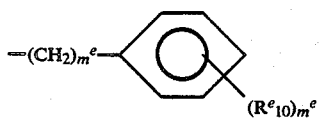

or the $R_{13}^e$ group join to complete an unsubstituted 5- or 6-membered ring or said ring in which one or more of the carbons has a lower alkyl of 1 to 4 carbons, or a di (lower alkyl of 1 to 4 carbons) substituent.

$R^e$ and $R_5^e$ are independently selected from hydroxy, lower alkoxy, di(lower alkyl)-amino-lower alkoxy, such as dimethylaminoethoxy, lower alkyl-carbonyl-amino-lower alkoxy, such as acetylaminoethoxy, lower alkyl-carbonyloxy-lower alkoxy, such as pivaloyloxymethoxy,

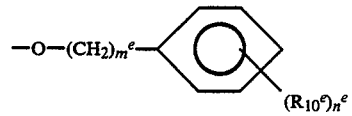

wherein $m^e$, $n^e$ and $R_{10}^e$ are as defined above, amino, lower alkyl-amino, di(lower alkyl)-amino, hydroxyamino, benzylamino, or phenethylamino.

$R_1^e$ is hydrogen, lower alkyl.

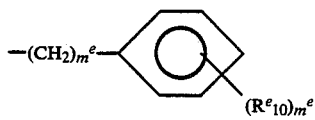

halo substituted lower alkyl, hydroxy substituted lower alkyl, $-(CH_2)_8^e$—cycloalkyl, $-(CH_2)_9^e$—carboxy, $-(CH_2)_9^e$—S-lower alkyl,

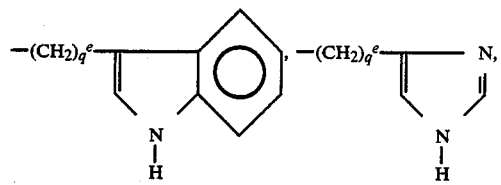

$-(CH_2)_q^e$-guanidinyl, $-(CH_2)_q^e$—NH$_2$, $-(CH_2)_q^e$—N(lower alkyl)$_2$,

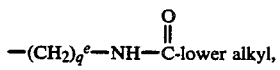

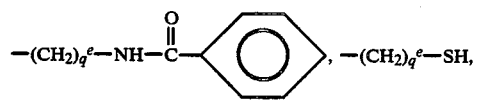

$-(CH_2)_q^e$-lower alkoxy, $-(CH_2)_q^e$—O—

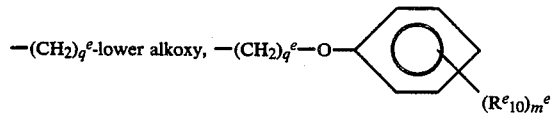

$-(CH_2)_q^e$—C-lower alkoxy, or

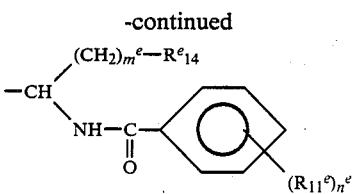

wherein $m^e$, $n^e$, $R_{10}^e$ and $R_{11}^e$ are as defined above, $R_{14}^e$ is lower alkyl, cycloalkyl, or and $o^e$ is

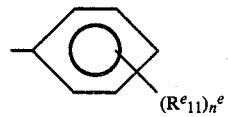

and $q^e$ is an integer from 1 to 4.

$R_2^e$ is hydrogen or lower alkyl.

$R_3^e$ is hydrogen, lower alkyl, halo substituted lower alkyl, hydroxy substituted lower alkyl, $-(CH_2)_9^e$—NH$_2$, $-(CH_2)_9^e$—q$^e$—, N-(lower alkyl)$_2$, $-(CH_2)_9^e$ guanidinyl, $-(CH_2)_9^e$—SH, $-(CH_2)_9^e$—S-lower alkyl,

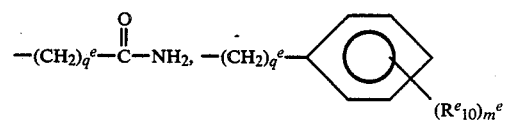

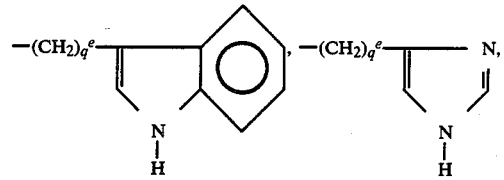

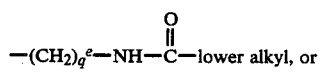

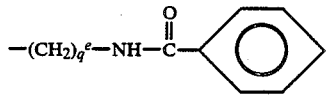

wherein $R_{10}^e$, $n^e$ and $q^e$ are defined above.

U.S. Pat. No. 4,470,973 to Natarajan et al discloses substituted peptides which are angiotensin converting enzyme inhibitors and have the formula

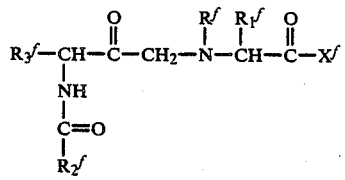

$X^f$ is an amino or imino acid of the formula

-continued
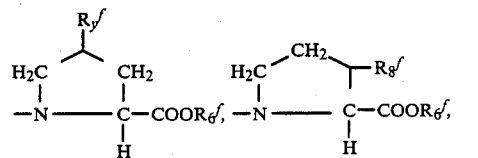
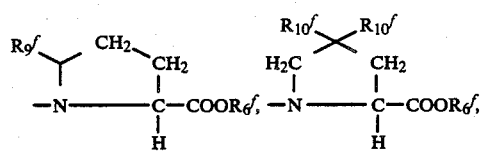
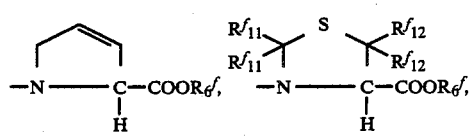
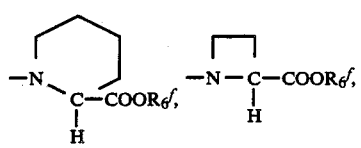
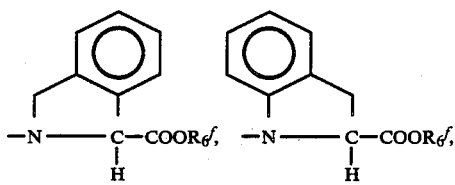
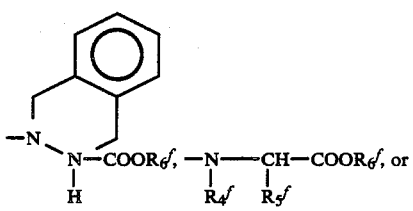
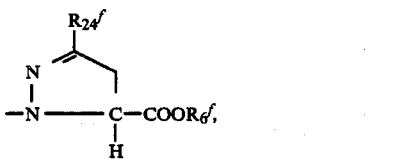
$R_7{}^f$ is hydrogen, lower alkyl, halogen, keto, hydroxy,
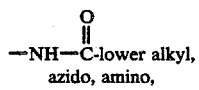
azido, amino,
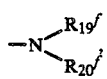
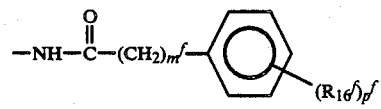
-continued
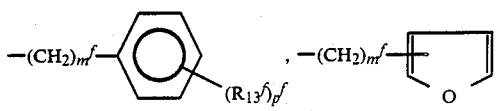
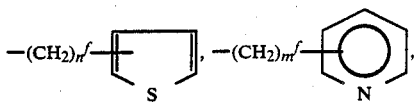
a 1- or 2-naphthyl of the formula
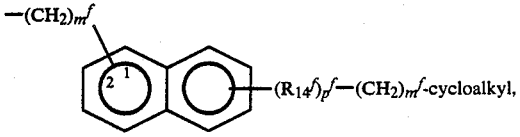
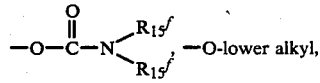
−O−(CH$_2$)$_m{}^f$
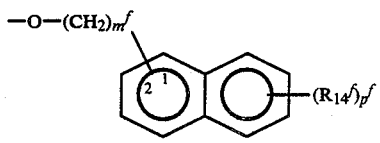
a 1- or 2-napthyloxy of the formula
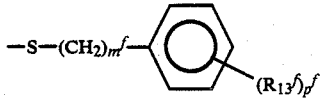
−S-lower alkyl,
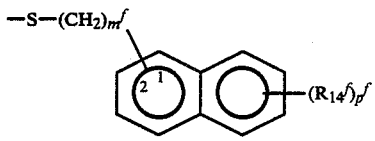
or a 1- or 2-naphthylthio of the formula
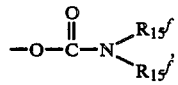
$R_8{}^f$ is keto, halogen,
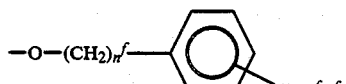
−O−lower alkyl, a 1- or 2-naphthyloxy of the formula
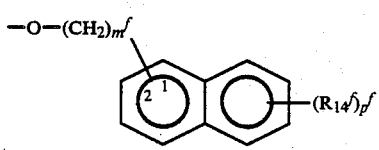

—S-lower alkyl,

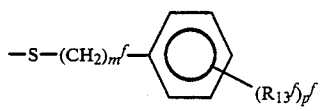

or a 1- or 2-naphthylthio of the formula

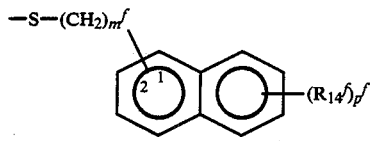

$R_9{}^f$ is keto of

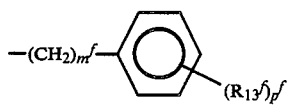

$R_{10}{}^f$ is halogen or —$Y^f$—$R_{10}{}^f$.

$R_{11}{}^f$, $R_{11'}{}^f$, and $R_{12'}{}^f$ are independently selected from hydrogen and lower alkyl or $R_{11}{}^f$, $R_{12}{}^f$ and $R_{12'}{}^f$ are hydrogen and $R_{11}{}^f$ is

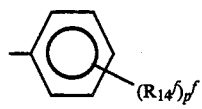

$R_{13}{}^f$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{14}{}^f$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

$m^f$ is zero, one, two, three, or four.

$p^f$ is one, two or three provided that p is more than one only if $R_{13}{}^f$ or $R_{14}{}^f$ is hydrogen, methyl, methoxy, chloro, or fluoro.

$R_{15}{}^f$ is hydrogen or lower alkyl of 1 to 4 carbons.

$Y^f$ is oxygen or sulfur.

$R_{16}{}^f$ is lower alkyl of 1 to 4 carbons,

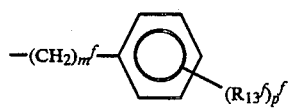

or the $R_{16}{}^f$ groups join to complete an unsubstituted 5- or 6-membered ring or said ring in which one or more of the carbons has a lower alkyl of 1 to 4 carbons or a di(lower alkyl of 1 to 4 carbons) substituent.

$R_4{}^f$ is hydrogen, lower alkyl,

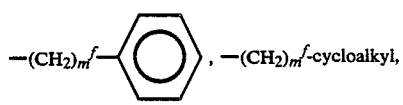

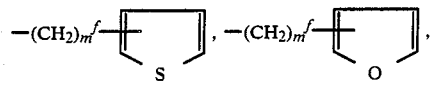

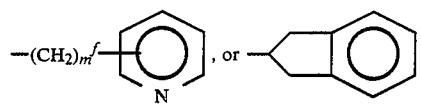

$R_5{}^f$ is hydrogen, lower alkyl,

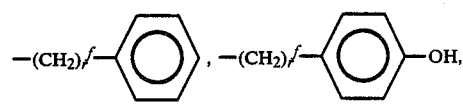

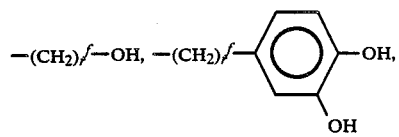

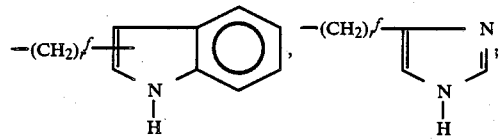

—$(CH_2)_r{}^f$—$NH_2$, —$(CH_2)_r{}^f$—$SH$, —$(CH_2)_r{}^f$—S-lower alkyl,

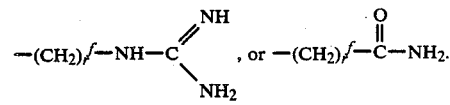

$r^f$ is an integer from 1 to 4.

$R_{19}{}^f$ is lower alkyl, benzyl, or phenethyl.

$R_{20}{}^f$ is hydrogen, lower alkyl, benzyl or phenethyl, $R^f$ is hydrogen, lower alkyl, cycloalkyl,

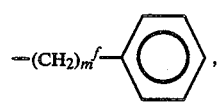

—$(CH_2)_2$—$NH_2$, —$(CH_2)_3$—$NH_2$, —$(CH_2)_4$—$NH_2$, —$(CH_2)_2$—OH, —$(CH_2)_3$—OH, —$(CH_2)_4$—OH, —$(CH_2)_2$—SH, —$(CH_2)_3$—SH, or —$(CH_2)_4$—SH.

$R_1{}^f$ is hydrogen, lower alkyl, halo substituted lower alkyl,

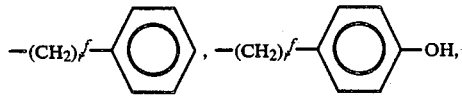

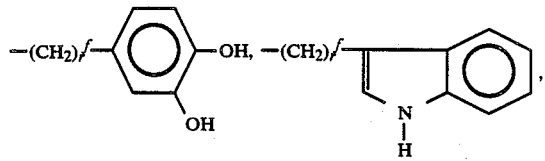

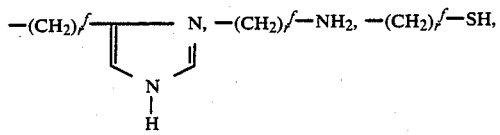

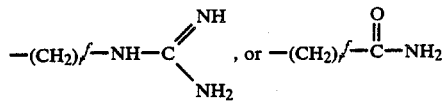

provided that $R_1^f$ is hydrogen only if $R^f$ is other than hydrogen.

$R_2^f$ is

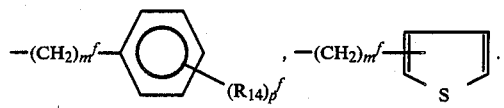

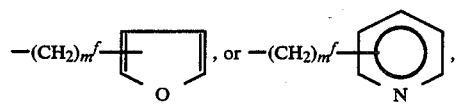

$R_3^f$ is hydrogen, lower alkyl,

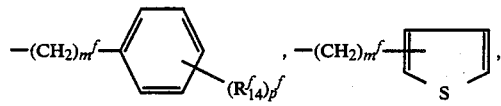

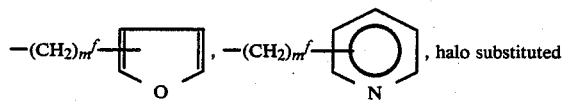, halo substituted lower alkyl, $-(CH_2)_{m^f}-$cycloalkyl, 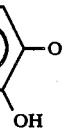

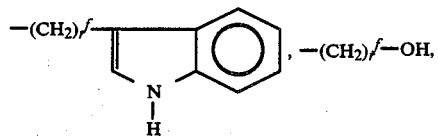

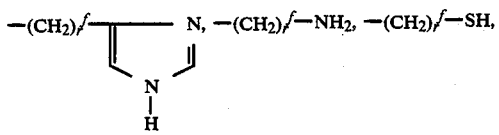

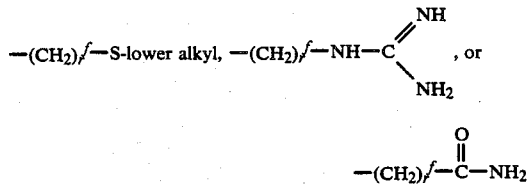

wherein $m^f$, $R_{14}^f$, $p^f$ and $r^f$ are as defined above.

$R_6^f$ is hydrogen, lower alkyl, benzyl, benzhydryl,

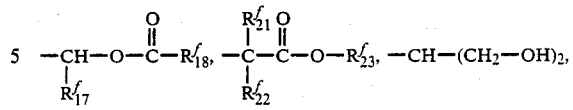

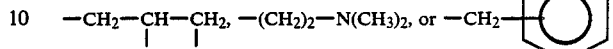

$R_{12}^f$ is hydrogen, lower alkyl, cycloalkyl, or phenyl.
$R_{18}^f$ is hydrogen, lower alkyl, lower alkoxy, or phenyl or $R_{17}^f$ and $R_{18}^f$ taken together are $-(CH_2)_2-$, $-(CH_2)_3-$, $-CH=CH-$, or

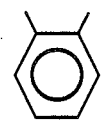

$R_{21}^f$ and $R_{22}^f$ are independently selected from hydrogen and lower alkyl.
$R_{23}^f$ is lower alkyl.
$R_{24}^f$ is hydrogen, lower alkyl,

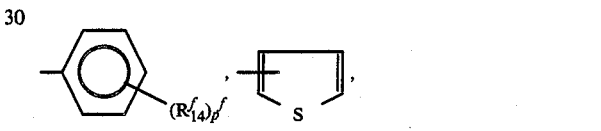

British Specification No. 2095682 published Oct. 6, 1982 discloses N-substituted-N-carboxyalkyl aminocarbonyl alkyl glycine derivatives which are said to be angiotensin converting enzyme inhibitors and have the formula

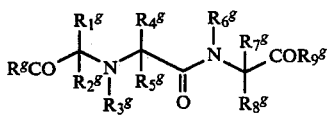

either
(A) $R^g$ and $R_9^g$ are OH, 1-6C alkoxy, 2-6C alkenyloxy, di-(1-6C alkyl)amino-(1-6C) alkoxy, 1-6C hydroxyalkoxy, acylamino-(1-6C) alkoxy, acyloxy-(1-6C)alkoxy, aryloxy, aryloxy-(1-6C)alkoxy, $NH_2$, mono- or di-(1-6C alkyl)amino, hydroxyamino or aryl-(1-6C)alkylamino;
$R_1^g$-$R_5^g$, $R_7^g$ and $R_8^g$ are 1-20C alkyl, 2-20C alkenyl, 2-20C alkynyl, aryl, aryl-(1-6C) alkyl having 7-12C or heterocyclyl-(1-6C)alkyl having 7-12C;
$R_6^g$ is cycloalkyl, polycycloalkyl, partly saturated cycloalkyl or polycycloalkyl, cycloalkyl-(1-6C)alkyl having 3-20C, 6-10C aryl, aryl-(1-6C)alkyl, aryl-(2-6C)alkenyl or aryl-(2-6) alkynyl; or
$R_2^g$ and $R_3^g$ together with the C and N atoms to which they are attached or $R_3^g$ and $R_5^g$ together with the N and C atoms to which they are attached form an N-heterocycle containing 3–5C or 2–4C and a S atom; all alkyl, alkenyl and alkynyl are optionally substituted by OH, 1–6C alkoxy, thio(sic), 1–6C alkylthio, $NH_2$, mono- or di(1–6C alkyl)amino, halogen or $NO_2$; all 'cycloalkyl' groups (including poly and partially unsaturated) are optionally substituted by halogen. 1–6C hydroxyalkyl, 1–6C alkoxy, amino-(1–6C alkyl) amino, di-(1–6C alkyl) amino, SH, 1–6C alkylthio, $NO_2$ or $CF_3$; and aryl groups are optionally substituted by OH, 1–6C alkoxy, $NH_2$, mono- or di-(1–6C alkyl) amino, SH, 1–6C alkylthio, 1–6C hydroxyalkyl, 1–6C aminoalkyl, 1–6C thioalkyl, $NO_2$, halogen, $CF_3$, $OCH_2O$, ureido or guanidino;

or (B) $R^g$ and $R_9^g$ are H or 1–6C alkoxy;

$R_1^g$ and $R_2^g$ are H, 1–6C alkyl, aryl-(1–6C) alkyl having 7–12C or heterocyclyl-(1–6C) alkyl having 6–12C;

$R_3^g$–$R_5^g$, $R_7^g$ and $R_8^g$ are H or 1–6C alkyl;

$R_6^g$ is cycloalkyl, polycycloalkyl partly saturated cycloalkyl or polycycloalkyl, cycloalkyl-(1–6C) alkyl having 3–20C, aryl or aryl-(1–6C) alkyl; and aryl has 6–10C and is optionally substituted by 1–6C alkyl, 2–6C alkenyl, 2–6C alkynyl, OH, 1–6C alkoxy, $NH_2$, mono- or di(1–6C alkyl) amino, SH, 1–6C alkylthio, 1–6C hydroxyalkyl, 1–6C aminoalkyl, 1–6C thioalkyl, $NO_2$, halogen, $CF_3$, $OCH_2O$, ureido or guanidino.

U.S. Pat. No. 4,470,972 to Gold et al discloses 7-carboxyalkyl-aminoacyl-1,4-dithia-7-azaspiro[4.4]nonane-8-carboxylic acids which are angiotensin converting enzyme inhibitors and have the formula

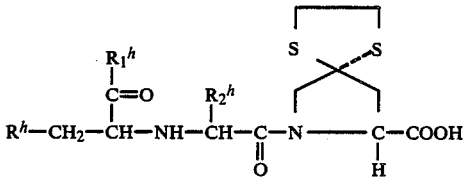

wherein $R^h$ is lower alkyl, benzyl, benzylthio, benzyloxy, phenylthio or phenoxy;

$R_1^h$ is hydroxy or lower alkoxy;

$R_2^h$ is hydrogen, lower alkyl or amino lower alkyl; and the pharmaceutcally acceptable salts thereof.

European patent application No. 0 050 800 published May 5, 1982 discloses carboxyalkyl dipetides derivatives which are said to be angiotensin converting enzyme inhibitors and have the formula

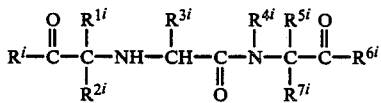

or a pharmaceutically acceptable salt thereof, wherein $R^i$ and $R^{6i}$ are the same or different and are hydroxy, lower alkoxy, lower alkenyloxy, dilower alkylamino lower alkoxy, acylamino lower alkoxy, acyloxy lower alkoxy, aryloxy, aryllower alkoxy, amino lower alkylamino, dilower alkylamino, hydroxyamino, aryllower alkylamino, or substituted aryloxy or substituted aryllower alkoxy wherein the substitutent is methyl, halo or methoxy; $R^{1i}$ is hydrogen, alkyl of from 1 to 10 carbon atoms, substituted lower alkyl wherein the substituent is hydroxy, lower alkoxy, aryloxy, substituted aryloxy, heteroaryloxy, substituted heteroaryloxy, amino, lower alkylamino, diloweralkylamino, acylamino, arylamino, substituted arylamino, guanidino, imidazolyl, indolyl, lower alkylthio, arylthio, substituted arylthio, carboxy, carbamoyl, lower alkoxy carbonyl, aryl, substituted aryl, aralkyloxy, substituted aralkyloxy, aralkylthio or substituted aralkylthio, wherein the aryl or heteroaryl portion of said substituted aryloxy, heteroaryloxy, arylamino, arylthio, aryl, aralkyloxy, aralkylthio group is substituted with a group selected from halo, lower alkyl, hydroxy, lower alkoxy, amino, aminomethyl, carboxyl, cyano, or sulfamoyl; $R^{2i}$ and $R^{7i}$ are the same or different and are hydrogen or lower alkyl; $R^{3i}$ is hydrogen, lower alkyl, phenyl lower alkyl, aminomethylphenyl lower alkyl, hydroxyphenyl lower alkyl, hydroxy lower alkyl, acylamino lower alkyl, amino lower alkyl, dimethylamino lower alkyl, guanidino lower alkyl, imidazolyl lower alkyl, indolyl lower alkyl, or lower alkyl thio lower alkyl; $R^{4i}$ and $R^{5i}$ are the same or different and are hydrogen, lower alkyl or $Z^i$, or $R^{4i}$ and $R^{5i}$ taken together form a group represented by $Q^i$, $U_i$, $V^i$, $Y^i$, $D^i$ or $E^i$, wherein;

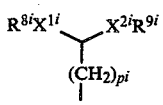

wherein $X^{1i}$ and $X^{2i}$ independent of each other are O, S or $CH_2$, $R^{8i}$ and $R^{9i}$ independent of each other are lower alkyl, lower alkenyl, lower alkynyl, cycloalkyl having 3 to 8 carbon atoms, hydroxy lower alkyl, or $-(CH_2)_{n^i}Ar^i$, wherein $N^i$ is 0, 1, 2 or 3 and $Ar^i$ is unsubstituted or substituted phenyl, furyl, thienyl or pyridyl, wherein said substituted phenyl, furyl, thienyl or pyridyl groups are substituted with at least one group that is independently selected from $C_1$ to $C_4$ alkyl, lower alkoxy, lower alkylthio, halo, $CF_3$ and hydroxy, or $R^{8i}$ and $R^{9i}$ taken together form a bridge $W^i$, wherein $W^i$ is a single bond or a methylene bridge or a substituted methylene bridge when at least one of $X^{1i}$ and $X^{2i}$ is methylene, or $W^i$ is an alkylene or substituted alkylene bridge having 2 or 3 carbon atoms, said substituted methylene bridge or said substituted alkylene bridge having one or two substituents selected from lower alkyl, aryl and aryl lower alkyl groups, and $p^i$ is 0, 1 or 2; with the proviso that at least one of $R^{4i}$ and $R^{5i}$ is $Z^i$, with the proviso that if $R^{4i}$ is $Z^i$ and $p^i$ is 0 then $X^{1i}$ and $X^{2i}$ must both be methylene, and with the proviso that if $X^{1i}$ and $X^{2i}$ are both methylene then $R^{8i}$ and $R^{9i}$ must form an alkylene bridge $W^i$;

$Q^i$ is

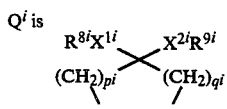

wherein $R^{8i}$, $R^{9i}$, $X^{1i}$ and $X^{2i}$ are as defined above, $p^i$ is 0, 1 or 2, $q^i$ is 0, 1 or 2, with the proviso that the sum of $p^i$ and $q^i$ must be 1, 2 or 3, with the proviso that if $p^i$ is 0 then $X^{1i}$ and $X^{2i}$ must be methylene, and with the proviso that if $X^{1i}$ and $X^{2i}$ are methylene then $R^{8i}$ and $R^{9i}$ taken together form a bridge $W^i$, wherein $W^i$ is as defined above;

$V^i$ is

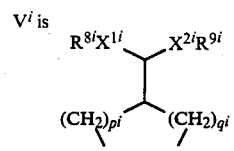

wherein $R^{8i}$, $R^{9i}$, $X^{1i}$ and $X^{2i}$ are as defined above, $p^i$ is 0, 1 or 2 and $q^i$ is 0, 1 or 2, with the proviso that the sum of $p^i$ and $q^i$ is 1, 2 or 3, with the proviso that if $X^{1i}$ and $X^{2i}$ are $CH_2$ then $R^{8i}$ and $R^{9i}$ taken together form a bridge $W^i$, wherein $W^i$ is as defined above;

$u^i$ is

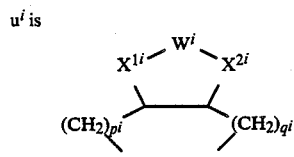

wherein $W^i$ is as defined above (except that $W^i$ may also be a methylene bridge when $X^{1i}$ and $X^{2i}$ are oxygen or sulfur), $X^{1i}$ and $X^{2i}$ are as defined above, $p^i$ is 0, 1 or 2, $q^i$ is 0, 1 or 2, with the proviso that the sum of $p^i$ and $q^i$ is 1 or 2, and with the proviso that if $p^i$ is 0, $X^{1i}$ must be $CH_2$;

$Y^i$ is

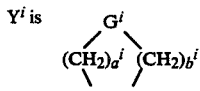

wherein $G^i$ is oxygen, sulfur or $CH_2$, $a^i$ is 2, 3, or 4 and $b^i$ is 1, 2, 3, 4 or 5, with the proviso that the sum of $a^i$ and $b^i$ is 5, 6 or 7 or $G^i$ is $CH_2$, $a^i$ is 0, 1, 2 or 3, $b^i$ is 0, 1, 2 or 3 with the proviso that the sum of $a^i$ and $b^i$ is 1, 2 or 3, with the proviso that the sum of $a^i$ and $b^i$ may be 1, 2 or 3 only if $R^{1i}$ is lower alkyl substituted with aralkylthio or aralkyloxy;

$D^i$ is

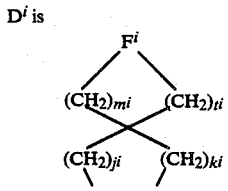

wherein $F^i$ is O or S, $j^i$ is 0, 1 or 2 and $k^i$ is 0, 1 or 2, with the proviso that the sum of $j^i$ and $k^i$ must be 1, 2 or 3, and $m^i$ is 1, 2 or 3 and $t^i$ is 1, 2 or 3, with the proviso that the sum of $m^i$ and $t^i$ must be 2, 3 or 4;

$E^i$ is

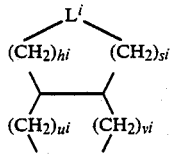

wherein $L^i$ is O or S, $u^i$ is 0, 1 or 2 and $v^i$ is 0, 1 or 2, with the proviso that the sum of $u^i$ and $v^i$ must be 1 or 2, and $h^i$ is 1 or 2 and $s^i$ is 1 or 2, with the proviso that the sum of $h^i$ and $s^i$ must be 2 or 3.

European patent application No. 0 037 231 published Oct. 7, 1981 discloses acyl derivatives of octahydro-1H-indole-2-carboxylic acids which are said to be angiotensin converting enzyme inhibitors and have the formula

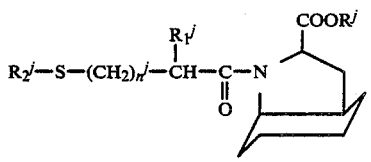

wherein $R^j$ is hydrogen or lower alkyl; $R_1^j$ is hydrogen, lower alkyl, or benzyl; $R_2^j$ is hydrogen or

wherein $R_3^j$ is lower alkyl, heteroaryl containing 4 to 9 carbon atoms and one or two nitrogen, oxygen or sulfur atoms; phenyl, substituted phenyl have 1 or 2 substituents selected from the group consisting of fluorine, chlorine, bromine, lower alkyl or alkoxy; and n is 0 or 1; wherein lower alkyl and lower alkoxy include straight or branched groups containing 1 to 4 carbon atoms, and pharmaceutically acceptable salts of the compounds when $R^j$ is hydrogen and when $R_3^j$ is heteroaryl containing 1 or 2 nitrogen atoms, Also disclosed are substituted acyl compounds of octahydro-1H-indole-2-carboxylic acid having the formula

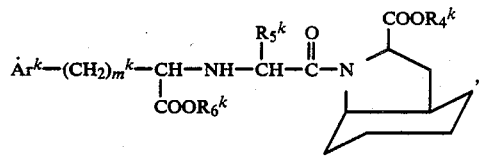

wherein $R_4^k$ is hydrogen or lower alkyl; $R_5^k$ is hydrogen, lower alkyl or benzyl; $R_6^k$ is hydrogen or lower alkyl; $Ar^k$ is phenyl or phenyl substituted with 1 or 2 substituents selected from the group consisting of fluorine, chlorine, bromine, lower alkyl, lower alkoxy, hydroxy or amino; and m is 0 to 3; wherein lower alkyl and lower alkoxy contain 1 to 4 straight or branched carbon atoms; and the pharmaceutcally acceptable salts thereof.

European patent application No. 0 079 522 published May 25, 1983 discloses N-carboxymethyl(amino)lysl-proline compounds which are said to be angiotensin converting enzyme inhibitors and have the formula where $$R^{1l}-CH(COOR^l)-NH-C(R^{2l})(H)-CO-N(A^l)-CH(COOR^l) \quad (I)^l$$

and $$R^{1l}-CH(COOR^l)-NH-C(R^{2l})(H)-CO-N(R^{3l})-CHR^{14l}(COOR^l) \quad (Ia)^l$$

wherein:

$R^l$ and $R^{2l}$ are independently hydrogen; loweralkyl; aralkyl; or aryl;

$R^{1l}$ is hydrogen; branched or straight chain $C_{1-12}$ alkyl and alkenyl; $C_3-C_9$ cycloalkyl and benzofused alkyl; substituted loweralkyl where the substitutents are halo, hydroxy loweralkoxy, aryloxy, amino, mono- or diloweralkylamino, acylamino, arylamino, guanidino, mercapto, loweralkylthio, arylthio, carboxy, carboxamido, or loweralkoxycarbonyl; aryl; substituted aryl where the substituents are loweralkyl, loweralkoxy, or halo; arloweralkyl; arloweralkenyl; heteroarloweralkyl; heteroarloweralkenyl; substituted arloweralkyl, substituted arloweralkenyl, substituted heteroarloweralkyl, or substituted heteroarloweralkenyl where the aryl and heteroaryl substituents are halo, dihalo, loweralkyl, hydroxy, loweralkoxy, amino, aminoloweralkyl, acylamino, mono- or diloweralkylamino, carboxyl, haloloweralkyl, nitro, cyano, or sulfonamido, and where the loweralkyl portion of arloweralkyl may be substituted by amino, acylamino, or hydroxyl;

$$-N(A^l)-CH(COOR^l) \text{ is } -N(X^l-Y^l)-C(ROOC)(R^{4l})-(CH)_{n^l},$$

$$-N(W^l)(R^lOOC-Z^l-)\text{-phenyl-}R^{6l} \text{ or}$$

$$-N(W^l)(COOR^l-Z^l-)\text{-cycloalkyl}(_{)n^l}$$

where $X^l$ and $Y^l$ taken together are $-CH_2-CH_2-$;

$$-CH(R^{5l})-S-;\ -C(=O)-CH_2-;\ -CH_2-C(=O)-;\ -C(=O)-O-;$$

$$-C(=O)-S-;\ -CH_2-CH(OR^{4l})-;\ -C(=O)-N(R^{4l})-;\text{ or }-CH_2-C(R^{4l})(R^{5l})-;$$

$R^{4l}$ is hydrogen; loweralkyl; aryl; substituted aryl;
$R^{5l}$ is hydrogen; loweralkyl; aryl or substituted aryl;
$n^l$ is 1 to 3;
$w^l$ is absent; $-CH_2-$;

or $-C(=O)-$; $-(CH_2)_{m^l}-$, where m is 0 to 2, provided that $m^l$ may not be 0 and $W^l$ may not be absent at the same time; and
$R^{6l}$ is hydrogen; loweralkyl; halo; or $OR^{4l}$;
$R^{2l}$ is $-(CH_2)_{r^l}-B^l-(CH_2)_{s^l}-NR^{7l}R^{15l}$ where
$r^l$ and $s^l$ are independently 0 to 3;
$B^l$ is absent; $-O-$; $-S-S$; or $-NR^{8l}-$; where $R^{8l}$ is hydrogen; loweralkyl; alkanoyl; or aroyl; and
$R^{7l}$ is $$-C(=NR^{11l})-R^{9l};\ -C(=NR^{11l})-NHR^{10l};\text{ or }-C(=N-J^l)(-K^l)-R^{12l}$$

where
$R^{9l}$ is loweralkyl; aralkyl; aryl; heteroaryl; or heteroarloweralkyl and these groups substituted by hydroxy, lower alkoxy or halo; carboxyl; carboxamido; nitromethenyl.
$R^{10l}$ is hydrogen; loweralkyl; aryl; or amidino;
$R^{11l}$ is hydrogen; loweralkyl cyano; amidino; aryl; aroyl; loweralkanoyl;

$-C(=O)-NHR^{13l}$; $-C(=O)-OR^{13l}$;

$-NO_2$; $-SO_2NH_2$; or $SO_2R^{13l}$;
$R^{12l}$ is hydrogen; loweralkyl; halo; aralkyl; amino; cyano; mono-or diloweralkylamino; or $OR^{4l}$;
$R^{13l}$ is hydrogen; loweralkyl; or aryl;
$R^{15l}$ is hydrogen; lower alkyl; aralkyl; or aryl;

$$-C(=N-J^l)(-K^l)-R^{12l}$$

constitute a basic heterocycle of 5 or 6 atoms or benzofused analogs thereof and optionally containing 1-3 N atoms, an oxygen, a sulfur, an S=O, or an $SO_2$ group and optionally substituted by amino, lower alkyl amino, diloweralkyl amino, lower alkoxy, or aralkyl groups;
$R^{3l}$ is $C_{3-8}$ cycloalkyl and benzofused $C_{3-8}$ cycloalkyl; perhydrobenzofused $C_{3-8}$ cycloalkyl; aryl; substituted aryl; heteroaryl; substituted heteroaryl;
$R^{14l}$ is hydrogen or loweralkyl; and,
a pharmaceutically acceptable salt thereof.

U.S. Pat. No. 4,256,761 to Suh et al discloses amides which are angiotensin converting enzyme inhibitors and have the general formula

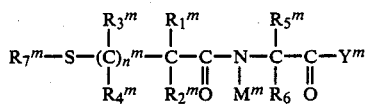

wherein
$R_1^m$, $R_2^m$, $R_3^m$, $R_4^m$ $R_5^m$ and $R_6^m$ are hydrogen, alkyl, alkenyl, alkynyl, phenyl-alkyl, and cycloalkyl, and may be the same or different,
$n^m$ is an integer from 0 to 4 inclusive,
$M^m$ is alkenyl, alkynyl, cycloalkyl, cycloalkyl-alkyl, polycycloalkyl, polycycloalkyl-alkyl, aryl, aralkyl, heteroaryl, heteroaryl-alkyl, hetero-cycloalkyl, hetero-cycloalkyl-alkyl, fused aryl-cycloalkyl, fused aryl-cycloalkyl-alkyl, fused heteroaryl-cycloalkyl, fused heteroaryl-cycloalkyl-alkyl, alkoxyalkyl, alkylthioalkyl, alkylamino-alkyl, or dialkylaminoalkyl,
$Y^m$ is hydroxy, alkoxy, amino, or substituted amino, aminoalkanoyl, aryloxy, aminoalkoxy, or hydroxyalkoxy, and
$R_7^m$ is hydrogen, alkanoyl, carboxyalkanoyl, hydroxyalkanoly, aminoalkanoyl, cyano, amidino, carbalkoxy, $Z^mS$ or

wherein $Z^m$ is hydrogen, alkyl, hydroxyalkyl, or the radical

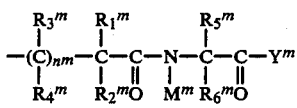

wherein $R_1^m$, $R_2^m$, $R_3^m$, $R_4^m$, $R_5^m$, $R_6^m$, $n^m$, $M^m$ and $Y^m$ are as described above; and where Y is hydroxy, their non-toxic, pharmaceutically acceptable alkali metal, alkaline earth metal, and amine salts.

U.S. Pat. No. 4,344,949 to Hoefle et al discloses acyl derivatives of 1,2,3,4-tetrahydroisoquinoline-3-carboxylic acid compounds which are angiotensin converting enzyme inhibitors and have the formula

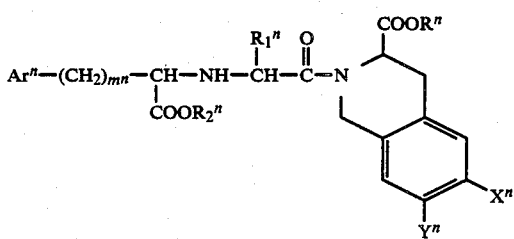

wherein $R^n$ is hydrogen, lower alkyl or aralkyl; $R_1^n$ is hydrogen, lower alkyl, or benzyl; $R_2^n$ is hydrogen or lower alkyl, and $Ar^n$ is phenyl or phenyl substituted with 1 or 2 substituents selected from the group consisting of fluorine, chlorine, bromine, lower alkyl, lower alkoxy, hydroxy or amino; $X^n$ and $Y^n$ are independently hydrogen, lower alkyl, lower alkoxy, lower alkylthio, lower alkylsulfinyl, lower alkylsulfonyl, hydroxy, or $X^n$ and $Y^n$ together are methylenedioxy; $m^n$ is 0 to 3; and the pharmaceutically acceptable acid salts thereof.

European Pat. No. 79022 published May 18, 1983 discloses N-amino acyl-azabicyclooctane carboxylic acid derivatives which have the formula

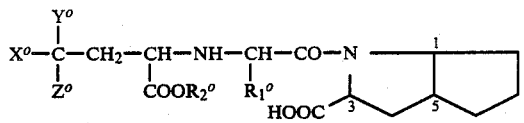

hydrogen atoms are ring positions 1 and 5 are cis to each other and the 3-carboxy group has the endo orientation;
$R_1^o$ is H, allyl, vinyl, or the side chain of an optionally protected naturally occurring a amino acid;
$R_2^o$ is H, 1-6C alkyl, 2-6C alkenyl or aryl (1-4C alkyl);
$Y^o$ is H or OH and $Z^o$ is H, or $Y^o$ and $Z^o$ together are oxygen;
$X^o$ is 1-6C alkyl, 2-6C alkenyl, 5-9C cycloalkyl, 6-12C aryl (optionally substituted by one to three 1-4C alkyl or alkoxy, OH, halo, nitro, amino (optionally substituted by one or two 1-4C alkyl), or methylenedioxy) or indol-3-yl.

European Pat. No. 46953 published Mar. 10, 1982 discloses N-amino acyl-indoline and tetrahydro isoquinoline carboxylic acids which are angiotensin coverting enzyme inhibitors and have the formula

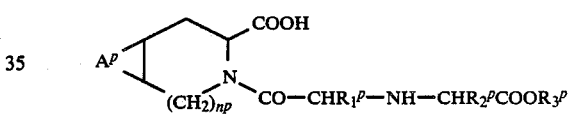

$n^p$ is 0 or 1;

is a benzene or cyclohexane ring:
$R_1^p$ and $R_2^p$ are each 1-6C alkyl, 2-6C alkenyl, 5-7C cycloalkyl, 5-7C cycloalkenyl, 7-12C cycloalkylalkyl, optionally partially hydrogenated 6-10C aryl, 7-14C aralkyl or 5-7 membered monocyclic or 8-10 membered bicyclic heterocyclyl containing 1 or 2 S or O and/or 1-4N atoms; all $R_1^p$ and $R_2^p$ groups are optionally substituted.
$R_3^p$ is H, 1-6C alkyl, 2-6C alkenyl or 7-14C aralkyl.
Preferred $R_1^p$ is Me and $R_2^p$ is phenethyl optionally substituted by halogen, Me or OMe.

For purposes of the invention, the preferred ACE inhibitor is 7-[N-(1(S)-carboxy-3-phenylpropyl)-(S)-alanyl]-1,4-dithia-7-azaspiro[4.4]nonane-8(S)-carboxylic acid.

It is believed that any ACE inhibitor will possess the novel utility described herein; however, for purposes of the present invention the preferred ACE inhibitors are compounds which are capable of inhibiting the action of ACE by at least 50 % at a concentration of 1 μM or less when tested by the following standard method:

ACE activity is determined by spectrophotometric assay of the product of the hydrolysis of the synthetic substrate, hippuryl histidyl leucine (HHL), as described by Cushman and Cheung, Biochem. Pharmacol., 20, 1637 (1971). The ACE used is prepared in a manner similar to that of Cheung and Cushman, Biochem. Biophys. Acta., 293, 451 (1973). Incubation for ACE assays is carried out at 37° C. Each 0.25 ml assay mixture contains the following components: 100 mM potassium phosphate buffer containing 300 mM sodium chloride, 5 mM HHL and 1.87 mU enzyme at pH 8.3 and various concentrations of inhibitors. The enzyme reaction is terminated after 60 minutes by the addition of 0.25 ml of 1N HCl. Inhibitors are dissolved in appropriate solvents. Hippuric acid solution for a standard curve is prepared in a similar manner.

Each experiment involves replicate incubations for each condition to be studied. $IC_{50}$ values (the concentration required for the 50% inhibition of ACE activity) are derived from calculated regression lines. Each experiment utilizes multiple concentrations of inhibitor.

The ACE inhibitors of the invention may exist in isomeric form. The invention contemplates all such isomers both in pure form and admixture, including racemic mixtures.

Many ACE inhibitors are known in the art and may be prepared by known methods or by variations thereof. The following example illustrates the preparation of the preferred ACE inhibitor of the invention.

EXAMPLE 1

7-[N-(1(S)-Carboxy-3-phenylpropyl)-(S)-alanyl]-1,4-dithia-7-azaspiro[4.4]nonane-8(S)-carboxylic acid A. Dissolve 1-benzyloxycarbonyl-4-keto-(S)-proline (15.7 g, 60 mmol) in acetic acid (45 ml) and ethyl acetate (45 ml), add 1,2-ethanedithiol (6.2 g, 66 mmol) and stir under nitrogen. Add boron trifluoride etherate (redistilled) and stir 4 hours. Pour the reaction mixture into a mixture of water (175 ml) ethyl acetate (120 ml) and ether (60 ml). Wash the organic layer with water (3×175 ml) then extract twice with 1.0N sodium bicarbonate (150 ml, then 50 ml). Acidify the aqueous layer to pH 1 with concentrated hydrochloric acid, extract twice with ether (150 ml, then 50 ml). Wash the organic layer with brine, dry over anhydrous magnesium sulfate and concentrate in vacuo to obtain crude 7-benzyoxycarbonyl-1,4-dithia-7-azaspiro[4.4]-nonane-8(S)-carboxylic acid as an oil (16.1 g).

B. Dissolve the product of Step A in acetic acid (30 ml) by stirring under nitrogen. Add 23% hydrobromic acid in acetic acid (50 ml) stir 3 hours and dilute over 5 minutes with ether (320 ml). Filter the solid, wash twice with ether (2×150 ml) and air dry to obtain a purple powder.

Dissolve the crude product in boiling ethanol (120 ml), add Darco grade 6-60 (6 g), and filter hot, washing with 2×10 ml hot ethanol. Dilute the filtrate with ether (300 ml) and allow to stand one hour. Filter the resultant precipitate, wash with ether (2×50 ml), and air dry to give 1,4-dithia-7-azaspiro[4.4]nonane-8(S)-carboxylic acid hydrobromide as beige crystals.

C. (1)a. To a 5 L flask equipped with a magnetic stirrer, dropping funnel and nitrogen inlet tube, add a solution of 190 g (0.92 mole) of S-alanine benzyl ester p-toluenesulfonate and 258 g (0.734 mole) of ethyl 2-oxo-4-phenyl butanoate in 1.4 L of ethanol. Stir for 2 hours under nitrogen. Add a solution of 17.7 g (0.282 mole) of sodium cyanoborohydride in 550 mL of ethanol, with stirring, over 90 minutes. Stir the solution overnight and concentrate to dryness in vacuo at room temperature. Partition the residue between 500 mL of $H_2O$ and 2 L of ether. Dry the ether layer over $MgSO_4$ and filter. Add 1.3M ethereal HCl to pH 4. Remove the ether and excess HCl in vacuo at room temperature. Slurry the residue in 250 mL of ether and dilute with 750 mL of hexane. Decant the supernatant from the resulting precipitate and wash with two 300 mL portions of ether. Triturate the residue with 300 mL of ether and filter under $N_2$ to give 134 g of a white solid. Slurry the solid in ether and make basic with saturated aqueous $NaHCO_3$. Dry the organic layer over $MgSO_4$, filter and concentrate in vacuo at room temperature to give 135 g of N-(1-carboethoxy-3-phenylpropyl)-(S)-alanine benzyl ester as an amber oil.

Dissolve 135 g of the resultant amber oil in 510 ml of ethyl acetate and add a hot solution of 40.5 g maleic acid in 895 ml of ethyl acetate. Cool to room temperature, filter the resulting precipitate, and recrystallize the precipitate from ethyl acetate to give N-(1(S)-carboethoxy-3-phenylpropyl)-(S)alanine benzyl ester hemimaleate as a solid, m.p. 127°-128° C., $[\alpha]_D 26=0°(H_2O)$.

Slurry 7.0 g (0.015 mole) of the above product in ethyl acetate and adjust to pH 8 with saturated aqueous sodium bicarbonate. Wash the organic layer with saturated aqueous sodium chloride solution, dry over magnesium sulfate, filter, and concentrate in vacuo at room temperature to a colorless oil. Dissolve the resultant oil in 100 ml ethanol containing 0.7 g of 10% Pd/C and hydrogenate at 60 psi at room temperature for 2 hours. Filter and evaporate the solvent under vacuum at room temperature to obtain 4.0 g of N-(1(S)-carboethoxy-3-phenylpropyl)-(S)-alanine as a white solid, m.p. 147°-148° C., $[\alpha]_D 26+24.8°$ (methanol).

b. To a solution of the product of Step (1)a (8.93 g, 32 mmol) and N-hydroxysuccinimide (4.42 g, 38.4 mmol) in dry dimethylformamide (64 ml), add 1-(3-dimethylaminopropyl)-3-ethylcarbodiimide hydrochloride (7.3 g, 38.4 mmol) and stir for 12 hours. Pour the reaction mixture into ethyl acetate (320 ml), wash with water (100 ml), brine (100 ml), and dry the organic layer over anhydrous magnesium sulfate. Concentrate in vacuo to obtain N-[1(S)-ethoxycarbonyl-3-phenylpropyl]-(S)-alanine succinimidyl ester as an oil.

(2). Dissolve the product of Step (1)b and 1,4-dithia-7-azaspiro-[4.4]nonane-8(S)-carboxylic acid hydrobromide (Step B) (9.16 g, 32 mmol) in dimethylformamide (155 ml) and cool to 0°-5° C. Add triethylamine (8.9 ml, 64 mmol) dropwise over 5 minutes, and rinse the funnel with dimethylformamide (5 ml). Stir at room temperature for 16 hours, concentrate in vacuo to 50 ml and dilute with water (150 ml). Adjust the solution to pH 4.0 with 1N hydrochloric acid. Extract the resultant brown gum with ethyl acetate (4×100 ml), combine the extracts, wash with water (20 ml) then brine (20 ml) and dry the organic phase over anhydrous magnesium sulfate. Evaporate the solvent in vacuo to obtain 7-[N-(1(S)-carboethoxy-3-phenylpropyl)-(S)-alanyl]-1,4-dithia-7-azaspiro[4.4]nonane-8(S)-carboxylic acid as a brown oil.

To purify, dissolve the crude product (3.3 g) in methanol (10 ml), place on Sephadex LH-20 (2.5×55 cm column) and elute with methanol. Combine the desired fractions and evaporate the solvent in vacuo to give a solid white foam. Analytically pure material has an $[\alpha]_D 26 = -29.5°$ (ethanol).

D. Hydrolyze the product of Step C(2) (0.3 g) in methanol (30 ml) with 2.5N sodium hydroxide (2.0 ml) for 20 hours at room temperature. Concentrate the reaction mixture in vacuo at room temperature. Dissolve the resultant residue in water and place on Bio Rad AG-50W-X2 (100–200 mesh) resin in the hydrogen form. Elute with water (300 ml), then with 2% pyridine in water. Concentrate the desired eluant fractions to obtain the title compound, m.p. 115°–117° C., $[\alpha]_D 26 = -22.4°(H_2O)$; $+1.9°$ (ethanol).

While the mechanism by which corticosteroids provide anti-inflammatory activity is unknown, their ability to provide relief from inflammatory symptoms is widely recognized. See, for example, Haynes, R. C., Jr., and Murad, F., "Adrenocorticotropic Hormone; Adrenocortical Steroids and Their Synthetic Analogs, Inhibitors of Adrenocortical Steroid Biosynthesis" in The Pharmacological Basis of Therapeutics (ed., A. G. Gilman, L. S. Goodman, A. Gilman), Macmillan Publishing, New York, 1980, 6th ed., pp. 1470–1492, n.b. pg. 1490–1491.

The IOP lowering effects of the compositions of the invention may be measured by the procedure described in Watkins et al., *J. Ocular Pharmacol.*, 1, (2):161 (1985).

Preferred pharmaceutical compositions of the invention comprise the combination of an ACE inhibitor and a steroid in an ophthamologically acceptable carrier adapted for topical administration to the eye, such as solutions, suspensions, ointments and solid inserts. For solutions and suspensions, those skilled in the art will know that a particular dosage of active ingredient may be calculated if one assumes that one drop of solution is being administered and if one knows the concentration (w/v) of the particular solution that is being administered. Thus, one drop (1/20 ml) of a 0.25% solution (contains 2.5 mg of active per ml) is known to contain 0.125 mg or 125 μg of active.

Topical ophthalmic formulations of the invention may combine the following amounts of each constituent:

ACE inhibitor from 0.00001 to 1.0% (w/v) and especially 0.001 to 0.01% of medicament. An amount of ACE inhibitor from between 0.005 μg to 500 μg, preferably 0.005 μg to 50 μg, and especially 0.005 μg to 5 μg of the active composition is applied to the human eye once or twice daily as needed. Individual dosage requirements, i.e., the amount of each dose and the frequency of administration, will depend on the potency of the particular ACE inhibitor, the severity of the increase in IOP and the response of the patient.

Steroid from 0.05 to 1.50% (w/v) of medicament. An amount of steroid from between 20 μg to 600 μg of the active composition is applied to the human eye one or more times a day as needed. Individual dosage requirements, i.e. the amount of each dose and the frequency of administration, will depend on the potency of the particular steroid, the severity of the disease and the response of the patient. Appropriate dosage ranges for each steroid are well known to those skilled in the art. The particular steroid used will determine the ACE inhibitor chosen and the dosage of ACE inhibitor administered.

Each component may be administered separately, and separate administration is especially appropriate when the steroid is administered systemically or topically other than in an ophthamological composition, since topical ophthamological application of the ACE inhibitor is preferred. The concentration of the steroid in such systemic or topical compositions and the unit dosage weights thereof vary considerably, depending as above on such factors as the potency of the steroid, the severity of the disease and the response of the patient. Appropriate dosage ranges for systemic or topical administration of each steroid are well known in the art.

Since the present invention relates to treatment with a combination of an ACE inhibitor and a steroidal anti-inflammatory agent wherein the ACE inhibitor and steroid are administered separately, the invention also relates to combining separate pharmaceutical compositions in kit form, that is, combining two separate units, an ACE inhibitor pharmaceutical composition and a steroid pharmaceutical composition, in a single package. Preferred components of the kit comprise a topical ophthamological ACE inhibitor pharmaceutical composition and a pharmaceutically acceptable steroid composition. More preferred components of the kit are a topical ophthamological ACE inhibitor pharmaceutical composition and a topical ophthamological steroid pharmaceutical composition. A particular advantage of the more preferred embodiment of the kit resides in the ability to provide a combination of an ACE inhibitor composition which can be administered once or twice a day and a steroid composition which may be administered as frequently as once each hour.

Where utilized herein, the terms "controlling" and "suppressing" the elevated intraocular pressure mean the regulation, attenuation and modulation of increased intraocular tension. The term also means that the diminution in the otherwise elevated intraocular pressure obtained by the practice of the invention is maintained for a significant period of time as for example, between consecutive doses of the composition of the invention.

To prepare suitable dosage forms, the active compositions may be conveniently admixed with a non-toxic pharmaceutically acceptable carrier suitable for topical ophthalmolgic administration. Typical of such pharmaceutically acceptable carriers are, for example, water, mixtures of water and watermiscible solvents such as lower alkanols or vegetable oils, petroleum based jelly, and including also from 0.5 to 5% by weight of hyroxyethyl cellulose, ethyl oleate, carboxymethyl cellulose, polyvinylpyrrolidone, and other water soluble ophthalmologically acceptable non-toxic polymers, for example, cellulose derivatives such as methyl cellulose, alkali metal carboxymethyl cellulose, hydroxyethyl cellulose, hydroxyproply cellulose, hydroxypropylmethyl cellulose; acrylates such as polyacrylic acids salts, ethylacrylates; polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum and mixtures of these polymers. The pharmaceutical preparation may also contain non-toxic auxiliary substances such as emulsifying, preserving, wetting, bodying agents and the like, as for example, polyethylene glycols 200, 300, 400 and 600, carbowaxes 1,000, 1,500, 4,000, 6000 and 10,000, antibacterial components such as quarternary ammonium compounds; phenylmercuric salts known to have cold sterilizing properties and which are non-injurious in use; thimerosal, methyl and propyl paraben, benzyl alcohol, phenyl ethanol; buffering ingredients such as alkali metal chloride, borate, acetate, gluconate buffers; antioxidants such as sodium metabisulfite, butylated hydroxyanisol (BHA), butylated hydroxytoluene (BHT) and the like; and other conventional ingredients such as sorbitan monolaurate, triethanolamine oleate, polyoxyethylene sorbitan monopalmitylate, dioctyl alkali metal sulfosuccinate, monothioglycerol, ethylenediamine tetracetic acid and the like.

Additionally, suitable ophthalmic vehicles can be used as carrier media for the present purpose including conventional phosphate buffer vehicle systems, isotonic boric acid vehicles, isotonic alkali chloride vehicles, tris and the like.

The pharmaceutical preparation may also be in the form of a solid insert. For example, one may use a solid water soluble polymer as the carrier for the medicament. Inserts that are known in the art that are suitable for this use include those described in British Pat. No. 15611, and in U.S. Pat. Nos. 3,993,071; 3,986,510; 3,868,445; and 3,867,510. Solid water insoluble inserts, such as those prepared from ethylene vinyl acetate copolymer, may also be utilized.

The compositions of the invention may include additional therapeutic agents in addition to the ACE inhibitor and steroid. For example antibiotics, anesthetics as well as other IOP lowering agents may be present.

The above descriptions on pages 4–36, inclusive, of suitable classes of ACE inhibitors for use in the present invention were taken from the noted patents and publications or abstracts thereof. Reference should be made to such patents and publications themselves for their full disclosures of such classes and specific compounds within such classes, such patents and publications being incorporated herein by reference for such purposes, and as to any typographical errors or the like which may have occurred in transcription. Also, in describing such suitable ACE inhibitors the superscript letters a–p were included to distinguish among the various classes of compounds and the variable substituent groups thereof.

I claim:

1. A method for reducing and controlling the elevated intraocular pressure associated with the use of hydrocortisone which comprises administering the combination of an anti-inflammatory-effective amount of hydrocortisone in a pharmaceutically acceptable carrier and an intraocular pressure-lowering effective amount of an angiotensin converting enzyme inhibitor of the formula

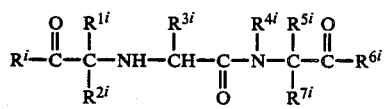

or a pharmaceutically acceptable salt thereof, where $R^i$ and $R^{6i}$ are the same or different and are hydroxy, lower alkoxy, lower alkenyloxy, dilower alkylamino lower alkoxy, acylamino lower alkoxy, acyloxy lower alkoxy, aryloxy, aryllower alkoxy, amino, lower alkylamino, dilower alkylamino, hydroxyamino, aryllower alkylamino, or substituted aryloxy or substituted aryllower alkoxy wherein the substitutent is methyl, halo or methoxy; $R^{1i}$ is hydrogen, alkyl of from 1 to 10 carbon atoms, substituted lower alkyl wherein the substitutent is hydroxy, lower alkoxy, aryloxy, substituted aryloxy, heteroaryloxy, substituted heteroaryloxy, amino, lower alkylamino, diloweralkylamino, acylamino, arylamino, substituted arylamino, guanidino, imidazolyl, indolyl, lower alkylthio, arylthio, substituted arylthio, carboxy, carbamoyl, lower alkoxy carbonyl, aryl, substituted aryl, aralkyloxy, substituted aralkyloxy, aralkylthio or substituted aralkylthio, wherein the aryl or heteroaryl portion of said substituted arylkoxy, heteroaryloxy, arylamino, arylthio, aryl, aralkyloxy, aralkylthio group is substituted with a group selected from halo, lower alkyl, hydroxy, lower alkoxy, amino, aminomethyl, carboxyl, cyano, or sulfamoyl; $R^{2i}$ and $R^{7i}$ are the same or different and are hydrogen or lower alkyl; $R^{3i}$ is hydrogen, lower alkyl, phenyl lower alkyl, aminomethylphenyl lower alkyl, hydroxyphenyl lower alkyl, hydroxy lower alkyl, acylamino lower alkyl, amino lower alkyl, dimethylamino lower alkyl, guanidino lower alkyl, imidazolyl lower alkyl, indolyl lower alkyl, or lower alkyl thio lower alkyl; $R^{4i}$ and $R^{5i}$ are the same or different and are hydrogen, lower alkyl or $Z^i$, or $R^{4i}$ taken together form a group represented by $Q^i$, $U^i$, $V^i$, $Y^i$, $D^i$ or $E^i$, wherein;

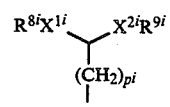

wherein $X^{1i}$ and $X^{2i}$ independent of each other are O, S or $CH_2$, $R^{8i}$ and $R^{9i}$ independent of each other are lower alkyl, lower alkenyl, lower alkynyl, cycloalkyl having 3 to 8 carbon atoms, hydroxy lower alkyl, or $-(CH_2)_{n}Ar^i$, wherein $n^i$ is 0, 1, 2 or 3 and $Ar^i$ is unsubstituted or substituted phenyl, furyl, thienyl or pyridyl, wherein said substituted phenyl furyl, thienyl or pyridyl groups are substituted with at least one group that is independently selected from $C_1$ to $C_4$ alkyl, lower alkoxy, lower alkylthio, halo, $CF_3$ and hydroxy, or $R^{8i}$ and $R^{9i}$ taken together form a bridge $W^i$, wherein $W^i$ is a single bond or a methylene bridge or a substituted methylene bridge when at least one of $X^{1i}$ and $X^{2i}$ is methylene, or $W^i$ is an alkylene or substituted alkylene bridge having 2 or 3 carbon atoms, said substituted methylene bridge or said substituted alkylene bridge having one or two substituents selected from lower alkyl, aryl and aryl lower alkyl groups, and $p^i$ is 0, 1 or 2; with the proviso that at least one of $R^4$ and $R^5$ is $Z^i$, with the proviso that if $R^4$ is $Z^i$ and $p^i$ is 0 then $X^{1i}$ and $X^{2i}$ must both be methylene, and with the proviso that if $X^{1i}$ and $X^{2i}$ are both methylene then $R^{8i}$ and $R^{9i}$ must form an alkylene bridge $W^i$;

$Q^i$ is

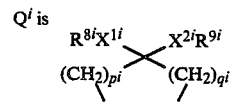

wherein $R^{8i}$, $R^{9i}$, $X^{1i}$ and $X^{2i}$ are as defined above, $p^i$ is 0, 1 or 2, $q^i$ is 0, 1 or 2, with the proviso that the sum of $p^i$ and $q^i$ must be 1, 2 or 3, with the proviso that if $p^i$ is 0 then $X^{1i}$ and $X^{2i}$ must be methylene, and with the proviso that if $X^1$ and $X^{2i}$ are methylene then $R^{8i}$ and $R^{9i}$ taken together form a bridge $W^i$, wherein $W^i$ is as defined above;

$V^i$ is

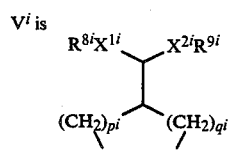

wherein $R^{8i}$, $R^{9i}$, $X^{1i}$ and $X^{2i}$ are as defined above, $p^i$ is 0, 1 or 2 and $q^i$ is 0, 1 or 2, with the proviso that the sum of $p^i$ and $q^i$ is 1, 2 or 3, with the proviso that if $X^{1i}$ and $X^{2i}$ are $CH_2$ then $R^{8i}$ and $R^{9i}$ taken together form a bridge $W^i$, wherein $W^i$ is as defined above;

$u^i$ is

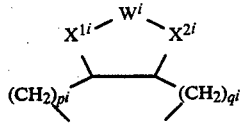

wherein $W^i$ is as defined above (except that $W^i$ may also be a methylene bridge when $X^{1i}$ and $X^{2i}$ are oxygen or sulfur), $X^{1i}$ and $X^{2i}$ are as defined above, $p^i$ is 0, 1 or 2, $q^i$ is 0, 1 or 2, with the proviso that the sum of $p^i$ and $q^i$ is 1 or 2, and with the proviso that if $p^i$ is 0, $X^{1i}$ must be $CH_2$;

$Y^i$ is

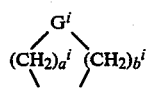

wherein $G^i$ is oxygen, sulfur or $CH_2$, $a^i$ is 2, 3 or 4 and $b^i$ is 1, 2, 3, 4 or 5, with the proviso that the sum of $a^i$ and $b^i$ is 5, 6 or 7 or $G^i$ $CH_2$, $a^i$ is 0, 1, 2 or 3, $b^i$ is 0, 1, 2 or 3 with the proviso that the sum of $a^i$ and $b^i$ is 1, 2 or 3, with the proviso that the sum of $a^i$ and $b^i$ may be 1, 2 or 3 only if $R^{1i}$ is lower alkyl substituted with aralkylthio or aralkyloxy;

$D^i$ is

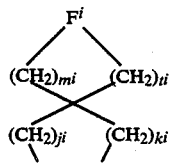

wherein $F^i$ is O or S, $j^i$ is 0, 1 or 2 and $k^i$ is 0, 1 or 2, with the proviso that the sum of $j^i$ and $k^i$ must be 1, 2 or 3, and $m^i$ is 1, 2 or 3 and $t^i$ is 1, 2 or 3, with the proviso that the sum of $m^i$ and $t^i$ must be 2, 3 or 4;

$E^i$ is

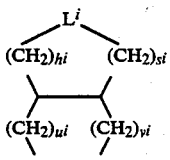

wherein $L^i$ is O or S, $u^i$ is 0, 1 or 2 and $v^i$ is 0, 1 or 2, with the proviso that the sum of $u^i$ and $v^i$ must be 1 or 2, and $h^i$ is 1 or 2 and $s^i$ is 1 or 2, with the proviso that the sum of $h^i$ and $s^i$ must be 2 or 3 in a topical ophthamological pharmaceutically acceptable carrier to a human in need of such treatment.

2. The method of claim 1 wherein hydrocortisone is administered in a topical, ophthmalogically acceptable carrier.

3. The method of claim 2 wherein the angiotensin converting enzyme inhibitor is 7-[N-(1(S)-carboxy-3-phenylpropyl]-(S)-alanyl]-1,4-dithia-7-azaspiro[4.4]nonane-8(S)-carboxylic acid.

4. A pharmaceutical composition useful for reducing and controlling the elevated intraocular pressure associated with the use of hydrocortisone which comprises:
 a. a pharmaceutically acceptable angiotensin converting enzyme inhibitor in an amount of from 0.005 mcg to 50 mcg per dose, wherein the angiotensin converting enzyme inhibitor is of the formula:

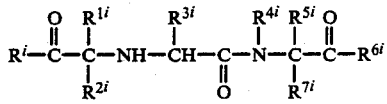

or a pharmaceutically acceptable salt thereof, wherein $R^i$ and $R^{6i}$ are the same or different and are hydroxy, lower alkoxy, lower alkenyloxy, dilower alkylamino lower alkoxy, acylamino lower alkoxy, acyloxy lower alkoxy, aryloxy, aryllower alkoxy, amino, lower alkylamino, dilower alkylamino, hydroxyamino, aryllower alkylamino, or substituted aryloxy or substituted aryllower alkoxy wherein the substitutent is methyl, halo or methoxy; $R^{1i}$ is hydrogen, alkyl of from 1 to 10 carbon atoms, substituted lower alkyl wherein the substitutent is hydroxy, lower alkoxy, aryloxy, substituted aryloxy, heteroaryloxy, substituted heteroaryloxy, amino, lower alkylamino, diloweralkylamino, acylamino, arylamino, substituted arylamino, guanidino, imidazolyl, indolyl, lower alkylthio, arylthio, substituted arylthio, carboxy, carbamoyl, lower alkoxy carbonyl, aryl, substituted aryl, aralkyloxy, substituted aralkyloxy, aralkylthio or substituted aralkylthio, wherein the aryl or heteroaryl portion of said substituted aryloxy, heteroaryloxy, arylamino, arylthio, aryl, aralkyloxy, aralkylthio group is substituted with a group selected from halo, lower alkyl, hydroxy, lower alkoxy, amino, aminomethyl, carboxyl, cyano, or sulfamoyl; $R^{2i}$ and $R^{7i}$ are the same or different and are hydrogen or lower alkyl; $R^{3i}$ is hydrogen, lower alkyl, phenyl lower alkyl, aminomethylphenyl lower alkyl, hydroxyphenyl lower alkyl, hydroxy lower alkyl, acylamino lower alkyl, amino lower alkyl, dimethylamino lower alkyl, guanidino lower alkyl, imidazolyl lower alkyl, indolyl lower alkyl, or lower alkyl thio lower alkyl; $R^{4i}$ and $R^{5i}$ are the same or different and are hydrogen, lower alkyl or $Z^i$, or $R^{4i}$ and $R^{5i}$ taken together form a group represented by $Q^i$, $U^i$, $V^i$, $Y^i$, $D^i$ or $E^i$, wherein;

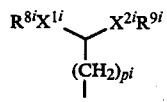

wherein $X^{1i}$ and $X^{2i}$ independent of each other are O, S or $CH_2$, $R^{8i}$ and $R^{9i}$ independent of each other are lower alkyl, lower alkenyl, lower alkynyl, cycloalkyl having 3 to 8 carbon atoms, hydroxy lower alkyl, or —$(CH_2)_n Ar^i$, wherein $n^i$ is 0, 1, 2 or 3 and $Ar^i$ is unsubstituted or substituted phenyl, furyl, thienyl or pyridyl, wherein said substituted phenyl furyl, thienyl or pyridyl groups are substituted with at least one group that is independently selected from $C_1$ to $C_4$ alkyl, lower alkoxy, lower alkylthio, halo, $CF_3$ and hydroxy, or $R^{8i}$ and $R^{9i}$ taken together form a bridge $W^i$, wherein $W^i$ is a single bond or a methylene bridge or a substituted methylene bridge when at least one of $X^{1i}$ and $X^{2i}$ is methylene, or $W^i$ is an alkylene or substituted alkylene bridge having 2 or 3 carbon atoms, said substituted methylene bridge or said substituted alkylene bridge having one or two substituents selected from lower alkyl, aryl and aryl lower alkyl groups, and $p^i$ is 0, 1 or 2; with the proviso that at least one of $R^4$ and $R^5$ is $Z^i$, with the proviso that if $R^4$ is $Z^i$ and $p^i$ is O then $X^{1i}$ and $X^{2i}$ must both be methylene, and with the proviso that if $X^{1i}$ and $X^{2i}$ are both methylene then $R^{8i}$ and $R^{9i}$ must form an alkylene bridge $W^i$;

$Q^i$ is

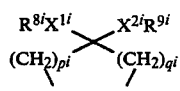

wherein $R^{8i}$, $R^{9i}$, $X^{1i}$ and $X^{2i}$ are as defined above, $p^i$ is 0, 1 or 2, $q^i$ is 0, 1 or 2, with the proviso that the sum of $p^i$ and $q^i$ must be 1, 2 or 3, with the proviso that if $p^i$ is 0 when $X^{1i}$ and $X^{2i}$ must be methylene, and with the proviso that if $X^1$ and $X^{2i}$ are methylene then $R^{8i}$ and $R^{9i}$ taken together form a bridge $W^i$, wherein $W^i$ is as defined above;

$V^i$ is

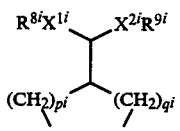

wherein $R^{8i}$, $R^{9i}$, $X^{1i}$ and $X^{2i}$ are as defined above, $p^i$ is 0, 1 or 2 and $q^i$ is 0, 1 or 2, with the proviso that the sum of $p^i$ and $q^i$ is 1, 2 or 3, with the proviso that if $X^{1i}$ and $X^{2i}$ are $CH_2$ then $R^{8i}$ and $R^{9i}$ taken together form a bridge $W^i$, wherein $W^i$ is as define above;

$u^i$ is

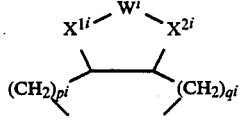

wherein $W^i$ is as defined above (except that $W^i$ may also be a methylene bridge when $X^{1i}$ and $X^{2i}$ are oxygen or sulfur), $X^{1i}$ and $X^{2i}$ are as defined above, $p^i$ is 0, 1 or 2, $q^i$ is 0, 1 or 2, with the proviso that the sum of $p^i$ and $q^i$ is 1 or 2, and with the proviso that if $p^i$ is 0, $X^{1i}$ must be $CH_2$;

$Y^i$ is

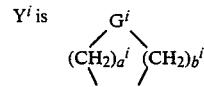

wherein $G^i$ is oxygen, sulfur or $CH_2$, $a^i$ is 2, 3 or 4 and $b^i$ is 1, 2, 3, 4 or 5, with the proviso that the sum of $a^i$ and $b^i$ is 5, 6 or 7 or $G^i$ is $CH_2$, $a^i$ is 0, 1, 2 or 3, $b^i$ is 0, 1, 2 or 3 with the proviso that the sum of $a^i$ and $b^i$ is 1, 2 or 3, with the proviso that the sum of $a^i$ and $b^i$ may be 1, 2 or 3 only if $R^{1i}$ is lower alkyl substituted with aralkylthio or aralkyloxy;

$D^i$ is

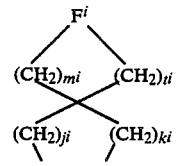

wherein $F^i$ is O or S, $j^i$ is 0, 1 or 2 and $k^i$ is 0, 1 or 2, with the proviso that the sum of $j^i$ and $k^i$ must be 1, 2 or 3, and $m^i$ is 1, 2 or 3 and $t^i$ is 1, 2 or 3, with the proviso that the sum of $m^i$ and $t^i$ must be 2, 3 or 4;

$E^i$ is

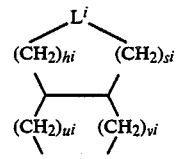

wherein $L^i$ is O or S, $u^i$ is 0, 1 or 2 and $v^i$ is 0, 1 or 2, with the proviso that the sum of $u^i$ and $v^i$ must be 1 or 2, and $h^i$ is 1 or 2 and $s^i$ is 1 or 2, with the proviso that the sum of $h^i$ and $s^i$ must be 2 or 3; and b. hydrocortisone in an amount of from 20 mcg to 600 mcg per dose;

in combination with a topical ophthamological pharmaceutically acceptable carrier.

5. A composition of claim 4 wherein the angiotensin converting enzyme inhibitor is 7-[N-(1(S)-carboxy-3-phenylpropyl)-S-alanyl]-1,4-dithia-7-azaspiro[4.4]nonane-8(S)-carboxylic acid.

* * * * *